(12) United States Patent
Brightbill

(10) Patent No.: US 8,465,469 B2
(45) Date of Patent: Jun. 18, 2013

(54) REINFORCED CATHETER AND METHODS OF MAKING

(75) Inventor: Jerry Brightbill, Newton, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1682 days.

(21) Appl. No.: 10/243,381

(22) Filed: Sep. 12, 2002

(65) Prior Publication Data

US 2004/0054349 A1   Mar. 18, 2004

(51) Int. Cl.
*A61M 25/00*      (2006.01)

(52) U.S. Cl.
USPC .......................................... 604/532; 604/510

(58) Field of Classification Search
USPC ............... 428/36.2–39.91, 35.9; 101/153, 101/170; 604/523–532, 95.01–95.05, 500–510; 156/154, 190, 117; 138/140–157
See application file for complete search history.

(56) References Cited

U.S. PATENT DOCUMENTS

| | | | |
|---|---|---|---|
| 3,998,602 A | 12/1976 | Horowitz et al. | |
| 4,082,621 A | 4/1978 | Spiliotis et al. | |
| 4,100,312 A | 7/1978 | Lombardo et al. | |
| 4,211,811 A | 7/1980 | Bordini et al. | |
| 4,374,709 A | 2/1983 | Combs | |
| 4,493,861 A | 1/1985 | Sirinyan et al. | |
| 4,520,046 A | 5/1985 | McCaskie et al. | |
| 4,547,193 A | 10/1985 | Rydell | |
| 4,560,445 A | 12/1985 | Hoover et al. | |
| 4,576,685 A | 3/1986 | Goffredo et al. | |
| 4,600,480 A | 7/1986 | Coombes et al. | |
| 4,663,199 A | 5/1987 | Liebler et al. | |
| 4,748,056 A | 5/1988 | Nuzzi et al. | |
| 4,790,831 A * | 12/1988 | Skribiski | 604/524 |
| 4,863,442 A * | 9/1989 | DeMello et al. | 604/527 |
| 4,895,739 A | 1/1990 | Bladon | |
| 4,952,357 A | 8/1990 | Euteneuer | |
| 5,007,990 A | 4/1991 | Bladon | |
| 5,101,682 A * | 4/1992 | Radisch et al. | 74/502.6 |
| 5,211,803 A | 5/1993 | Johnson et al. | |
| 5,217,440 A | 6/1993 | Frassica | |
| 5,275,597 A | 1/1994 | Higgins et al. | |
| 5,407,622 A | 4/1995 | Cleveland et al. | |
| 5,573,520 A | 11/1996 | Schwartz et al. | |
| 5,605,543 A | 2/1997 | Swanson | |
| 5,685,961 A * | 11/1997 | Pourrezaei et al. | 204/192.15 |
| 5,702,584 A | 12/1997 | Goenka et al. | |
| 5,725,510 A | 3/1998 | Hartmann et al. | |
| 5,725,513 A * | 3/1998 | Ju et al. | 604/527 |
| 5,741,429 A | 4/1998 | Donadio, III et al. | |
| 5,743,876 A | 4/1998 | Swanson | |
| 5,945,486 A | 8/1999 | Vargo et al. | |
| 5,951,881 A | 9/1999 | Rogers et al. | |

(Continued)

FOREIGN PATENT DOCUMENTS

WO   01/55473 A1   8/2001

*Primary Examiner* — Kevin C Sirmons
*Assistant Examiner* — Phillip Gray

(57) ABSTRACT

A reinforced catheter having a non-filamentous, seamless metal tube interposed between a polymeric hollow core and a polymeric outer jacket. The metal tube may have a pattern of apertures through which the hollow core and the polymeric outer jacket are adhered to each other. The invention also includes methods of making the reinforced catheter.

30 Claims, 4 Drawing Sheets

U.S. PATENT DOCUMENTS

| | | | |
|---|---|---|---|
| 5,991,650 A * | 11/1999 | Swanson et al. | 600/374 |
| 6,143,145 A | 11/2000 | Copping et al. | |
| 6,293,311 B1 * | 9/2001 | Bushi et al. | 138/138 |
| 6,605,399 B2 * | 8/2003 | Chowdry et al. | 430/62 |
| 2003/0082324 A1 * | 5/2003 | Sogard et al. | 428/36.9 |
| 2004/0103976 A1 * | 6/2004 | Busshoff et al. | 156/154 |

* cited by examiner

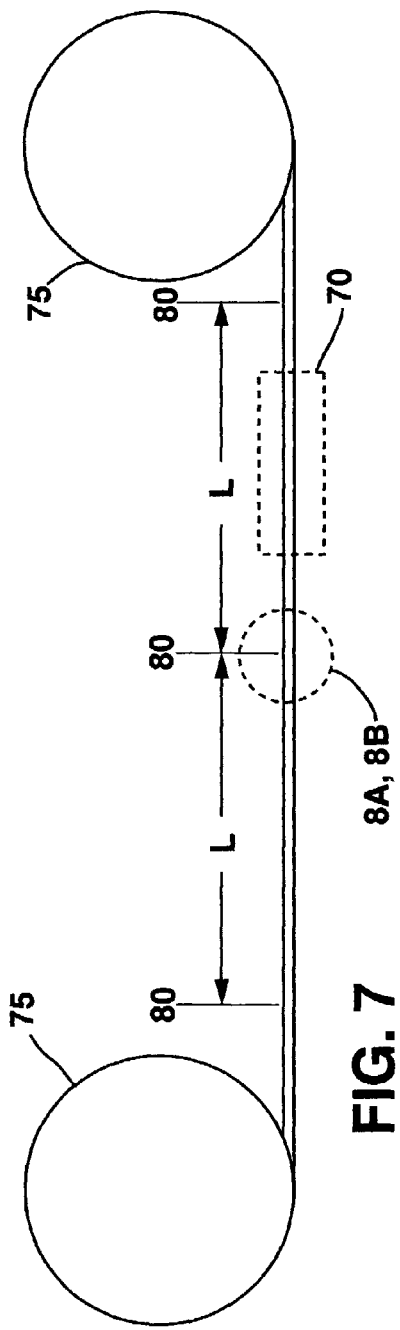
FIG. 7
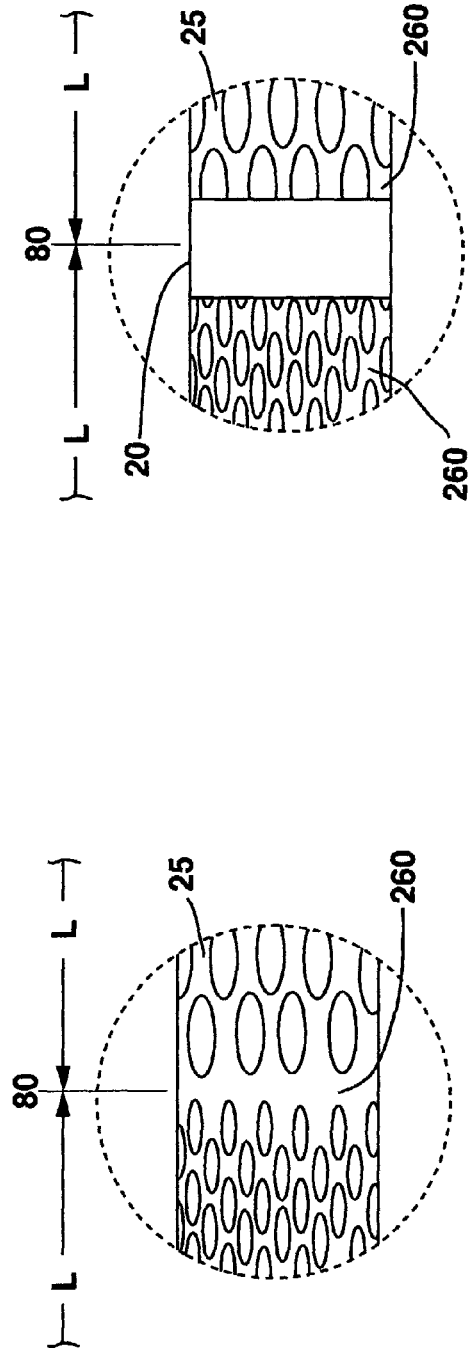
FIG. 8A
FIG. 8B

REINFORCED CATHETER AND METHODS OF MAKING

FIELD OF THE INVENTION

The present invention relates to reinforced catheters, and to methods of making the same. More particularly, the invention involves catheters used for accessing coronary, cerebral or other peripheral arteries for diagnostic or therapeutic procedures.

BACKGROUND OF THE INVENTION

Among the therapeutic procedures applicable to the present invention are percutaneous transluminal coronary angioplasty (PTCA) and stenting. These procedures can be used, for example, to reduce arterial build-up of cholesterol fats or atherosclerotic plaque. During such an intervention, a guiding catheter is used to form a direct conduit from outside a patient's body, through the vasculature to the site targeted for treatment or to the ostium of the diseased artery. Before performing an intervention, an angiography catheter may be utilized to diagnose the patient's symptoms by injecting radiopaque contrast into suspected arteries, creating fluoroscopic images.

Guiding catheters and angiography catheters must have sufficient bending stiffness to be pushed through vessels as well as sufficient torsional rigidity to provide a high degree of torsional control. It is also desirable for a catheter to have a soft or flexible distal tip to avoid dangers of puncturing or otherwise damaging a vessel as it twists through the vascular system. Examples of such soft tip catheters are known in the art. Guiding catheters and angiography catheters generally are formed as a three-layer composite tube. The first layer is a hollow liner, which, in the case of a guiding catheter, is provided with a lubricious inner surface to aid in device passage through the lumen of the catheter. The next layer is a reinforcing material, typically a stainless steel wire that is braided around the liner. An outer jacket encapsulates the braid and is bonded to the liner through braid interstices to create a monolithic structure from the three components.

The trend in the field of the invention has been toward catheters having thinner walls with a goal of providing a larger lumen, a smaller outside diameter, or both. While improvements in polymeric materials used for catheter liners and/or jackets have helped in the achievement of thinner walls, the thickness of the common braided reinforcement layer has become a limitation to further progress in this area. To create a woven braid, filaments must be passed over other filaments, giving the reinforcement layer, in effect, twice the thickness of the filaments. Additionally, despite their encapsulation between the outer jacket and the liner, braid filaments are not secured together at their intersections, so that the filaments can shift relative to each other, thus diminishing physical properties of the catheter such as torsional stiffness and kink resistance.

The prior art includes references that teach forming a catheter reinforcement layer by spirally wrapping a perforated film around a liner, or by rolling a patterned sheet to form a catheter tube. To create an uninterrupted layer of reinforcement material, such examples require a double-thickness overlapping seam or an unsecured butt seam, which has compromised physical properties. Thus, there is a continuing need for improvements in reinforced catheters having reduced wall thickness while maintaining good or improved properties of stiffness, torque transfer characteristics and high kink resistance.

SUMMARY OF THE INVENTION

The invention provides a reinforced catheter having a non-filamentous, seamless metal tube interposed between a polymeric hollow core and a polymeric outer jacket. The metal tube may have a pattern of apertures through which the hollow core and the polymeric outer jacket are adhered to each other. The metal tube forms a reinforcement layer that can be thinner than is practically achievable by known filamentous reinforcements.

BRIEF DESCRIPTION OF THE DRAWINGS

Features, aspects and advantages of the present invention will become better understood with reference to the following description, appended claims, and accompanying drawings where:

FIG. 7 illustrates, schematically, a reel-to-reel process of making catheter tubing in accordance with the present invention; and FIGS. 8A and 8B are enlarged views of the catheter tubing shown in FIG. 7, wherein a reinforcing layer has an aperture pattern that changes at spaced locations along the catheter tubing.

The drawings are not to scale.

DETAILED DESCRIPTION OF THE INVENTION

Figure 1:
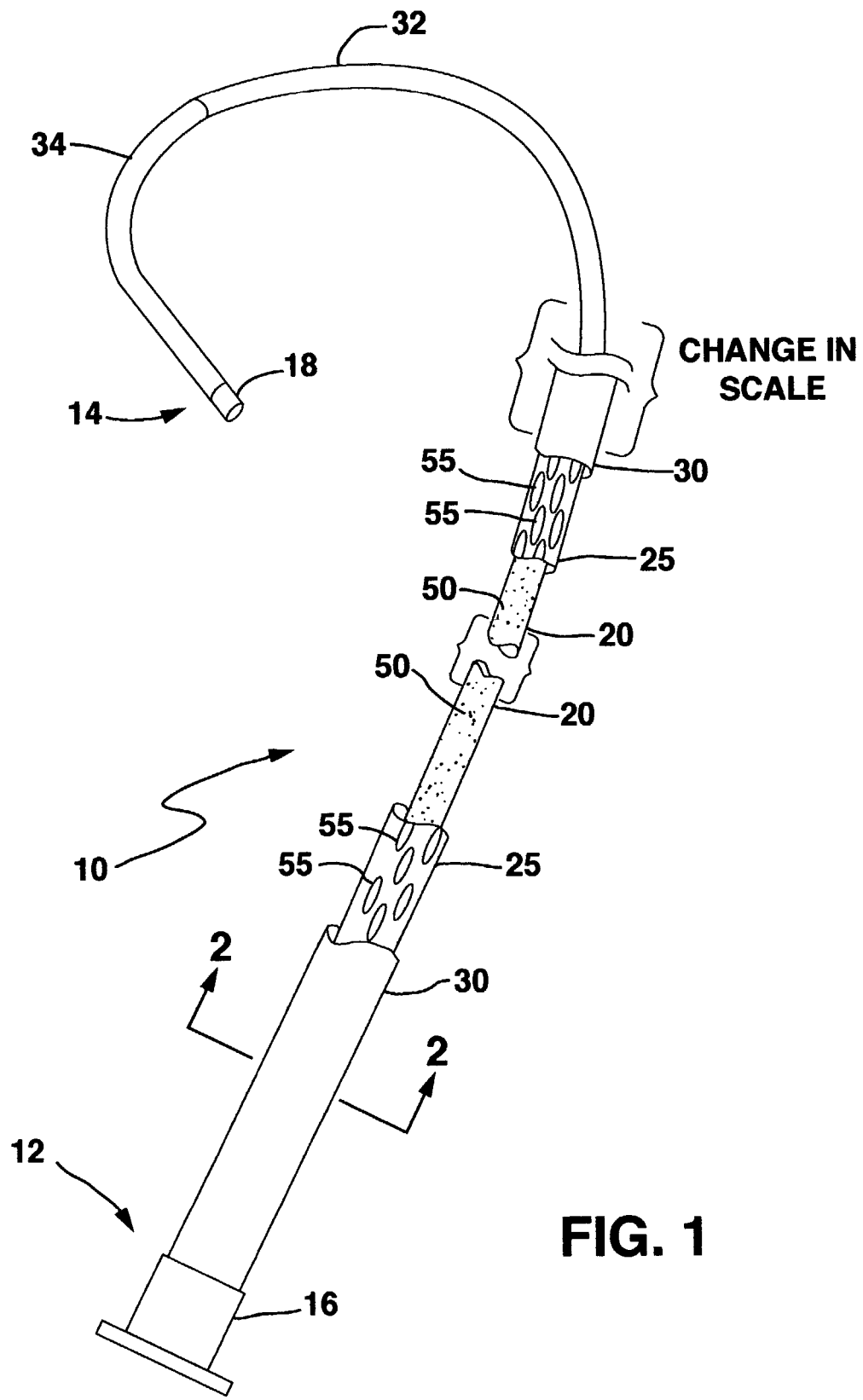
FIG. 1 shows a catheter in accordance with the present invention, wherein sections of layers have been removed for illustrative purposes.

FIG. 1 illustrates the invention as catheter 10 having proximal end 12 and distal end 14. Proximal end 12 has connector fitting 16 attached thereto, and distal end 14 is illustrated with optional soft tip 18. The partially sectioned portion of FIG. 1 illustrates three-layered construction of catheter 10, comprising hollow core 20, metal tube 25, and outer jacket 30.

FIG. 1 also shows an optional configuration of the invention wherein outer jacket 30 comprises proximal segment 32 and distal segment 34. The physical properties of distal segment 34 are different from the physical properties of proximal segment 32. For example, catheter 10 may become increasingly flexible in a distal direction by having distal segment 34 comprise a material that is softer than the material of proximal segment 32, and by having soft tip 18 comprise a material that is softer than the material of distal segment 34.

Figure 3:
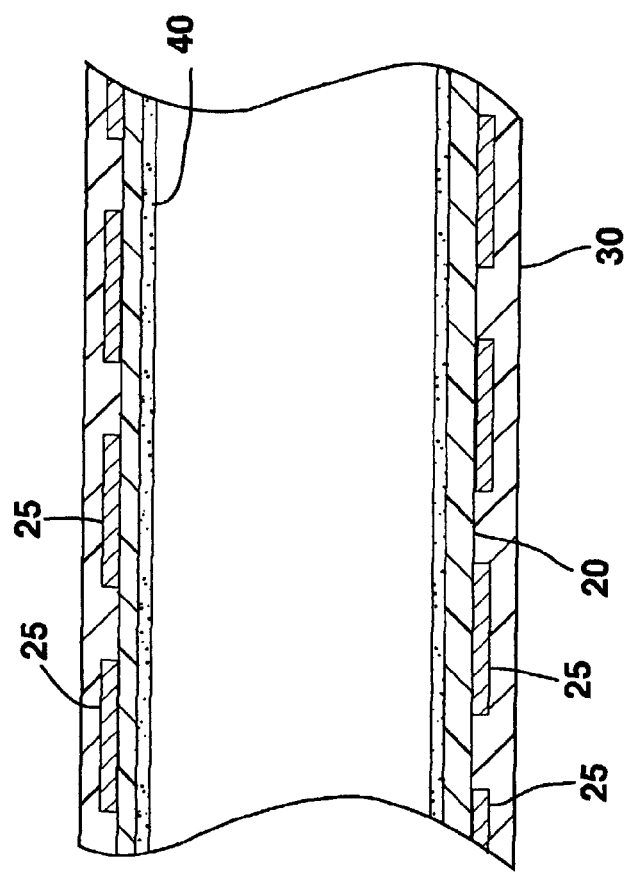
FIG. 3 is a longitudinal sectional illustration of a catheter in accordance with the present invention, taken along the line 3-3 of FIG. 2.
Figure 2:
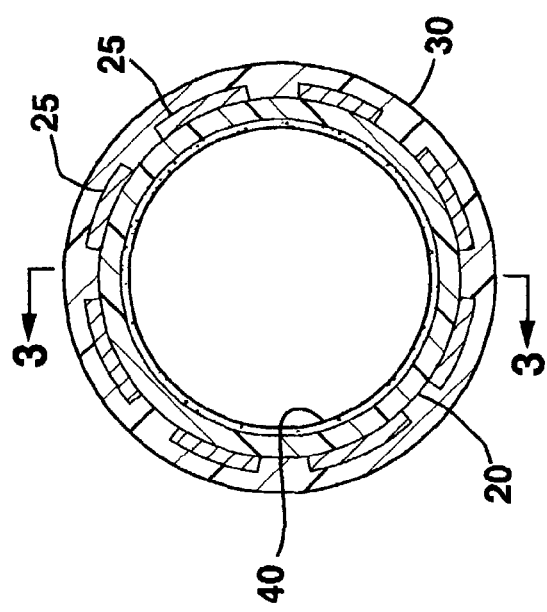
FIG. 2 is a transverse sectional illustration of a catheter in accordance with the present invention, taken along the line 2-2 of FIG. 1.

Hollow core 20 and/or outer jacket 30 may comprise polymeric materials such as polyolefins, thermoplastic polyurethanes, polyamides, thermoplastic elastomers, fluoropolymers, or blends, laminates, copolymers and/or block copolymers thereof. A polymer that is thermoplastically extrudable may be selected for advantages such as processing cost efficiency and the ability to be melt-bonded. Hollow core 20 may be extruded over a metal or plastic mandrel (not shown), which can be removed later during manufacturing. To make guiding catheters, it may be desirable to form hollow core 20 from a paste extrudable fluoropolymer such as polytetrafluoroethylene (PTFE), which provides a low friction surface for the catheter lumen. A slippery lumen can also be provided, however, by applying lubricious coating 40 to the inner surface of hollow core 20, as shown in FIGS. 2 and 3. Coating 40 may comprise silicone or hydrophilic compounds, or other materials well known to those of skill in the field of catheters, and it may be applied to fluoropolymers or other polymers.

Metal tube 25 is a non-filamentous, seamless reinforcement layer that has been formed on, and is adherent to the external surface of hollow core 20. The method of forming metal tube 25 may comprise a metallizing process such as electroplating, electroless plating, sputter coating, vapor deposition, or combinations thereof. Hollow core 20 may receive chemical or other surface treatments to enhance adhesion of metal tube 25 thereto, as will be understood by those familiar with techniques of metallizing plastics. Optionally, hollow core 20 may comprise a polymer matrix containing particles that act as metallizing nodes 50 when exposed at the external surface. Metal tube 25 may comprise a metal such as chromium, cobalt, gold, nickel, niobium, platinum, silver, stainless steel, tantalum, titanium, zirconium, or alloys and/or oxides thereof. Use of metal(s) having a relatively high x-ray frequency damping coefficient can enhance visualization of catheter 10 under fixed x-ray imaging or fluoroscopy, with attendant reduced requirements for radiopaque fillers in hollow core 20 or outer jacket 30.

Metal tube 25 may also have a pattern of apertures 55, through which hollow core 20 and outer jacket 30 may be adhered to each other, as shown in FIGS. 2 and 3. For example, outer jacket 30 may be formed about metal tube 25 by the process of thermoplastic extrusion, which includes forcing jacket material into apertures 55 and into melt-bonding contact with hollow core 20. Alternatively, outer jacket 30 may be compression molded around metal tube 25 by the use of shrink tubing, which can be removed afterwards. Apertures 55 may be formed in metal tube 25 by masking portions of hollow core 20 or otherwise selectively preventing the deposition of metal thereon.

Figure 4:
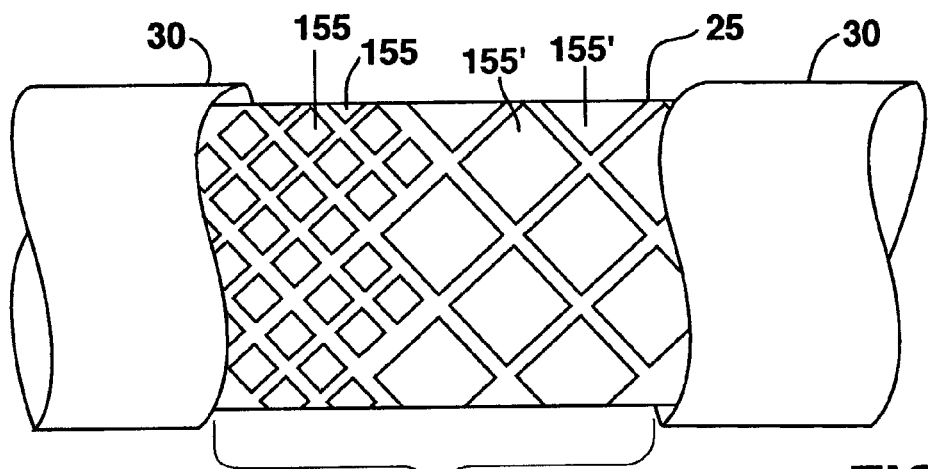
FIGS. 4-6 illustrate catheters in accordance with the present invention, wherein sections of the outer jacket have been removed to show a variety of aperture patterns in the reinforcement layer.
Figure 5:
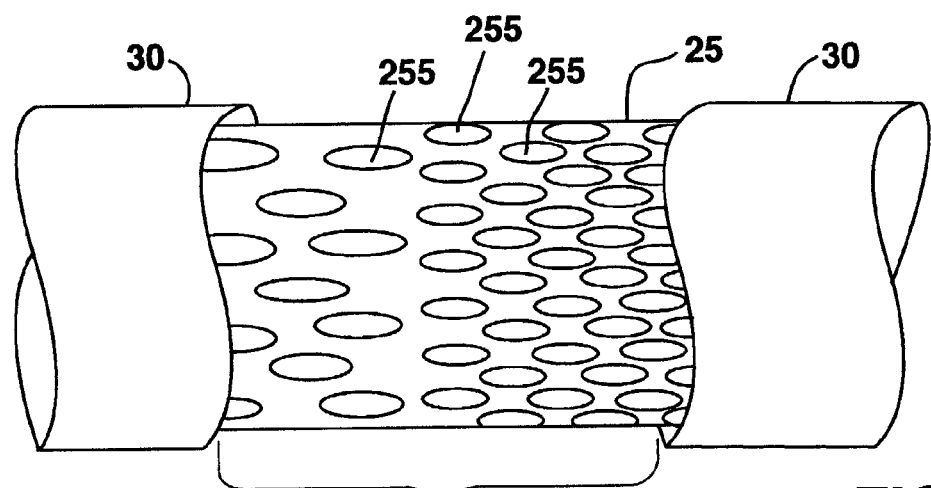
Figure 6:
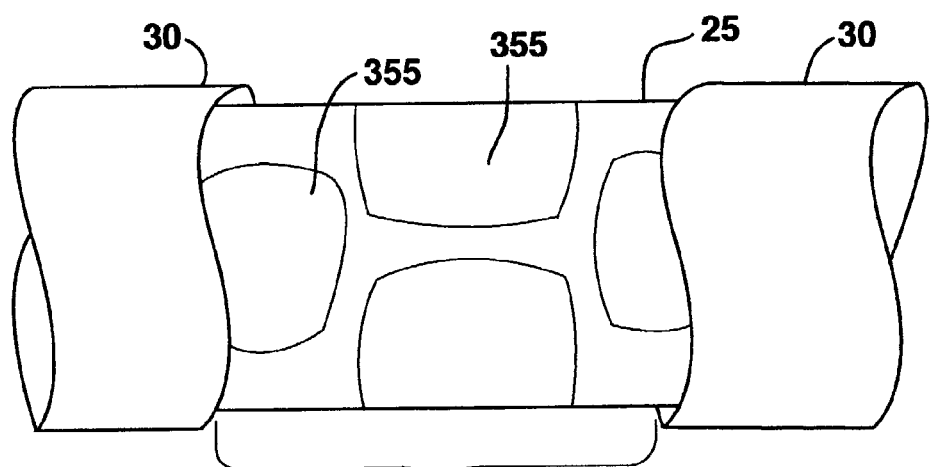

FIGS. 4-6 illustrate a variety of aperture patterns formed in metal tube 25, in accordance with the invention. In FIG. 4, apertures 155, 155' in pattern 160 are diamond-shaped, and pattern 160 varies to change the physical properties along the length of catheter 10. Pattern 160 may be considered to resemble the geometry of a variable-pitched braid used in known catheter constructions, and the crossed-helix configuration of pattern 160 may provide torque-transfer properties similar to those of a braid. However, pattern 160 has no overlapping double-thickness intersections. Furthermore, in pattern 160, the helical elements cannot shift with respect to each other because they are part of a unitary layer that constitutes metal tube 25. Such a built-in interlock feature permits metal tube 25 to be thinner than a conventional braided reinforcement layer while achieving comparable physical characteristics. The wall thickness of metal tube 25 may be about 0.051 mm (0.002 inch), about 0.025 mm (0.001 inch), about 0.013 mm (0.0005 inch) or less. The larger apertures 155' in pattern 160 provide decreased metal content and corresponding greater flexibility in comparison to smaller apertures 155. Apertures 155' may be disposed distal to apertures 155 to create a more flexible distal region of catheter 10.

In FIG. 5, apertures 255 in pattern 260 are oval or elliptical in shape and pattern 260 varies along catheter 10. In pattern 260, all apertures 255 are of the same size and shape, but the aperture spacing changes. In this case, the contracted aperture spacing decreases the metal content to create greater flexibility in selected, e.g. distal, portions of metal tube 25. Apertures 255 lack the sharp corners of apertures 155, 155', and may thereby avoid stress risers that could cause, under load conditions, premature fracturing of metal layer 25 and associated catheter kinking.

In FIG. 6, pattern 360 has circumferentially arranged pairs of large apertures 355. Adjacent pairs are staggered at 90° to create a highly flexible metal tube 25. Many other patterns are possible, including differently sized and shaped apertures, differently sized- and shaped spacing between apertures, pattern variations along the length of catheter 10, and the entire length or selected regions of metal tube 25 having no apertures.

A method of making catheter 10 is illustrated schematically in FIG. 7. Different processing steps can be performed at station 70 on an elongate work piece each time it is fed between reels 75. Optionally, multiple stations can be arranged in series (not shown) such that all necessary processing steps can be performed in a single pass between reels 75. Although the use of an elongate metal or plastic support mandrel is common to the process of making braid-reinforced catheters, the mandrel is merely an optional tool in the method of making the current invention. First, hollow core 20 is extruded, with or without a support mandrel. Next, metal tube 25 is formed on hollow core 20 by one of the metallizing processes discussed above. Apertures 55 may be formed in metal tube 25 by masking portions of hollow core 20 or otherwise selectively preventing the deposition of metal thereon. Next, outer jacket 30 is extruded over metal tube 25. If apertures 55 were formed in metal tube 25, then the extrusion of outer jacket 30 will force jacket material into apertures 55 and cause a melt-bond between outer jacket 30 and hollow core 20. Next, the composite catheter tubing is severed at cut points 80 into multiple sub-assemblies of intended catheter length L. Finally, catheters 10 are finished by securing connector fitting 16 to proximal end 12, and soft tip 18 to distal end 14. Additionally, guiding catheters and angiography catheters are typically formed with a heat-set curve adjacent distal end 14.

If it is desired to vary the pattern of apertures 55 along the length of catheter 10, then the pattern formed in metal tube 25 can be repeated or reversed every length L, as shown in FIGS. 8A and 8B. FIG. 8A shows cut point 80, located between repeats of aperture pattern 260. At cut point 80, a relatively contracted distal portion terminates and a relatively expanded proximal portion begins. FIG. 8B shows cut point 80, located between reversing aperture patterns 260. Relatively contracted distal portions of aperture pattern 260 abut each other at cut point 80. In the construction shown in FIG. 8B, cut points 80 alternate between abutting distal portions and abutting proximal portions (not shown).

Optionally, distal segment 34 may be formed in outer jacket 30 by removing a first jacket material of about the length of segment 34, then refilling the void with a second, different, e.g. softer, material. In a first alternative method of making catheter 10, outer jacket 30 can be applied after metal tube 25 has been formed around hollow core 20, and after multiple catheter sub-assemblies have been cut to length L. Unlike braided reinforcement layers, metal tube 25 will not tend to expand or unravel when it has been cut. In the first alternative method, catheter sub-assemblies can be fed individually through an extrusion "wire-head," or a pre-extruded tube can be radially compressed around the catheter sub-assembly by using a heat-shrink method. Additionally, distal segment 34 and/or other segments can be formed in catheter 10 by shrink-fitting different pre-extruded tubes around the catheter sub-assembly according to methods known by those of skill in the field of catheters.

According to a second alternative method, each catheter 10 is fabricated individually from the beginning, instead of using the above reel-to-reel method. This second alternative method is especially useful when hollow core 20 is made from a paste extrudable polymer such as PTFE, which has a finite extrudable length that is unsuitable for reel-to-reel catheter manufacturing. The processing steps and the order of operations are the same as those discussed above, except that any cutting step would only be required to trim individual sub-assemblies to length L.

While the invention has been particularly shown and described with reference to the preferred embodiments thereof, it will be understood by those skilled in the art that various changes in form and detail may be made therein without departing from the spirit and scope of the invention.

What is claimed is:

1. A reinforced catheter having proximal and distal ends, the catheter comprising:
    an elongate, flexible, polymeric, hollow tubular core extending between the proximal and distal ends of the catheter;
    the core having an outer surface with a tubular, seamless, metallized layer formed directly and adherent thereon of between 0.0005 and 0.002 inches thickness to define a reinforcement layer to enhance the ability of the catheter to transmit controllably to the distal end rotation applied to the proximal end; the reinforcement layer extending from the catheter proximal end to the catheter distal end and
    a flexible, polymeric jacket surrounding and fully covering the reinforcement layer and extending from the catheter proximal end to the catheter distal end.

2. The catheter according to claim 1, wherein the metal tube has a pattern of apertures, and the hollow core and the jacket are adhered to each other through the apertures.

3. The catheter according to claim 2, wherein the pattern of apertures varies between the catheter proximal and distal ends.

4. The catheter according to claim 3, wherein the apertures adjacent the catheter distal end are larger in size than the apertures adjacent the catheter proximal end.

5. The catheter according to claim 3, wherein the apertures adjacent the catheter distal end are larger in number than the apertures adjacent the catheter proximal end.

6. The catheter according to claim 1, wherein the metal tube has a wall thickness of about 0.051 mm (0.002 inch) or less.

7. The catheter according to claim 1, wherein the metal tube has a wall thickness of about 0.025 mm (0.001 inch) or less.

8. The catheter according to claim 1, wherein the metal tube has a wall thickness of about 0.013 mm (0.0005 inch) or less.

9. The catheter according to claim 1, wherein the tube comprises a metal selected from the group consisting of chromium, cobalt, gold, nickel, niobium, platinum, silver, stainless steel, tantalum, titanium, zirconium, or alloys and/or oxides thereof.

10. The catheter according to claim 1, wherein the hollow core comprises a polymeric material selected from the group consisting of polyolefins, thermoplastic polyurethanes, polyamides, thermoplastic elastomers, fluoropolymers, or blends, laminates, copolymers and/or block copolymers thereof.

11. The catheter according to claim 1, wherein the jacket comprises a polymeric material selected from the group consisting of polyolefins, thermoplastic polyurethanes, polyamides, thermoplastic elastomers, fluoropolymers, or blends, laminates, copolymers and/or block copolymers thereof.

12. The catheter according to claim 11, wherein the jacket further comprises multiple segments axially arranged along the catheter, each segment having physical properties that are different from the physical properties of an adjacent segment.

13. The catheter according to claim 12, wherein a first segment comprising a first material is disposed distal to a second segment comprising a second material, the first material being more flexible than the second material.

14. The catheter according to claim 1, further comprising a lubricious coating applied to an inner surface of the hollow core.

15. The catheter according to claim 1, further comprising a connector fitting mounted at the catheter proximal end.

16. The catheter according to claim 1, wherein a distal portion of the catheter is curved.

17. The catheter according to claim 1 being sufficiently flexible to be translocated through a curvaceous passageway within a patient.

18. The catheter according to claim 1 being capable of transmitting to the distal end substantially all rotation applied to the proximal end.

19. The catheter according to claim 1, wherein the metal tube has been formed on an outer surface of the hollow core by a metallizing process selected from the group consisting of electroplating, electroless plating, sputter coating, vapor deposition, or combinations thereof.

20. A method of making a reinforced catheter tubing, the catheter having proximal and distal ends comprising:
    providing an elongate, flexible, polymeric hollow core;
    forming a seamless metal tube having a wall thickness of 0.0005 to 0.002 inch directly on and adherent to the entire length of an outer surface of the hollow core by a metallizing process selected from the group consisting of electroplating, electroless plating, sputter coating or vapor deposition, the metal tube having a pattern of apertures, the configuration and thickness of the metal tube enhancing the ability of the catheter to transmit controllably to the distal end rotation applied to the proximal end; and
    forming a flexible, polymeric jacket fitted tightly about the entire length of the metal tube and being adhered to the hollow core through the apertures.

21. The method of claim 20, further comprising:
    removing a first material from a segment of the formed jacket; and
    filling the segment with a second material having physical properties different from those of the first material.

22. The method of claim 20, wherein forming the jacket comprises extruding a layer of polymeric material over the metal tube and hollow core.

23. The method of claim 20, further comprising:
    cutting the catheter tubing into sub-assemblies having an intended catheter-length.

24. The method of claim 23, wherein forming the jacket comprises shrink-fitting a length of polymeric tubing around the metal tube and hollow core after cutting the catheter tubing into sub-assemblies.

25. The method of claim 24, wherein the jacket comprises multiple segments axially arranged along each of the catheter sub-assemblies, each segment having physical properties that are different from the physical properties of an adjacent segment.

26. The method of claim 23, wherein the pattern of apertures varies along the catheter tubing, the pattern repeating or reversing at longitudinally sequential locations defined by the intended catheter-length.

27. The method of claim 20, wherein the hollow core comprises metallizing nodes.

28. The method of claim 20, wherein forming a metal tube comprises treating the hollow core to prevent metallization on areas having been selected to define the apertures.

29. A reinforced catheter having proximal and distal ends, the catheter comprising:
- an elongate, flexible, polymeric hollow core extending between the proximal and distal ends of the catheter;
- a tubular metal reinforcement layer electroplated or electroless plated or sputter coated or vapor deposited on an external surface of the hollow core, the reinforcement layer extending from the catheter proximal end to the catheter distal end; and
- a flexible, polymeric jacket surrounding the reinforcement layer and extending from the catheter proximal end to the catheter distal end;
- wherein the hollow core comprises a polymeric material selected from the group consisting of polyolefins, thermoplastic polyurethanes, polyamides, thermoplastic elastomers, fluoropolymers, or blends, laminates, copolymers and/or block copolymers thereof; and
- wherein the selected polymeric material contains particles capable of acting as metallizing nodes when exposed at the outer surface of the hollow core.

30. A reinforced catheter having proximal and distal ends, the catheter comprising:
- an elongate, flexible, polymeric hollow tubular core extending from the catheter proximal end to the catheter distal end;
- a seamless metal tube electroplated or electroless plated or sputter coated or vapor deposited directly on and adhered to an external surface of the hollow core and having a thickness of 0.002 inches or less to reinforce the catheter from the catheter proximal end to the catheter distal end to enhance the ability of the catheter to transmit controllably to the distal end rotation applied to the proximal end; and
- a flexible, polymeric jacket surrounding the metal tube and extending from the catheter proximal end to the catheter distal end, the jacket fully covering the reinforcement tube; and
- a connector fitting attached to the catheter proximal end.

* * * * *